(12) United States Patent
Deshmukh et al.

(10) Patent No.: US 9,862,718 B2
(45) Date of Patent: Jan. 9, 2018

(54) SODIUM SALT OF (2S, 5R)-6-BENZYLOXY-7-OXO-1,6-DIAZA-BICYCLO [3.2.1] OCTANE-2-CARBOXYLIC ACID AND ITS PREPARATION

(71) Applicant: WOCKHARDT LIMITED, Aurangabad (IN)

(72) Inventors: Vikas Vitthalrao Deshmukh, Ahmednagar (IN); Amit Chandra Mishra, Lucknow (IN); Dattatraya Vitthal Wani, Jalgaon (IN); Prasad Keshav Deshpande, Aurangabad (IN); Satish Bhavsar, Aurangabad (IN); Ravindra Dattatraya Yeole, Aurangabad (IN); Mahesh Vithalbhai Patel, Aurangabad (IN)

(73) Assignee: WOCKHARDT LIMITED, D-4 MIDC Area Chikalthana, Aurangabad (IN)

( * ) Notice: Subject to any disclaimer, the term of this patent is extended or adjusted under 35 U.S.C. 154(b) by 0 days.

(21) Appl. No.: 14/770,960

(22) PCT Filed: Oct. 10, 2013

(86) PCT No.: PCT/IB2013/059264
§ 371 (c)(1),
(2) Date: Aug. 27, 2015

(87) PCT Pub. No.: WO2014/135929
PCT Pub. Date: Sep. 12, 2014

(65) Prior Publication Data
US 2016/0002236 A1   Jan. 7, 2016

(30) Foreign Application Priority Data

Mar. 8, 2013   (IN) .......................... 699/MUM/2013

(51) Int. Cl.
*C07D 471/08*  (2006.01)

(52) U.S. Cl.
CPC .............................. *C07D 471/08* (2013.01)

(58) Field of Classification Search
None
See application file for complete search history.

(56) References Cited

U.S. PATENT DOCUMENTS

| 7,112,592 B2 * | 9/2006 | Lampilas | C07D 487/08 514/300 |
| 2012/0165533 A1 * | 6/2012 | Abe | C07D 211/60 546/121 |

OTHER PUBLICATIONS

Peterson et al., Iterative High-Throughput Polymorphism Studies on Acetaminophen and an Experimentally Derived Structure for Form IIIAm. Chem. Soc., 124, 10958-10959, 10958 (2002).
Morissette et al., High-throughput crystallization: Polymorphs, salts, co-crystals and solvates of pharmaceutical solidsAdvanced Drug Delivery Reviews, 56, 275-300, 296 (2004).
Buar et al., Disappearing Polymorphs Revisited (pp. 6972-6993)Angew. Chem. Int. Ed., 54, 6972-6993 (2015).

\* cited by examiner

*Primary Examiner* — Noble E Jarrell
(74) *Attorney, Agent, or Firm* — Bio Intellectual Property Services LLC; O. (Sam) Zaghmout

(57) ABSTRACT

Sodium salt of (2S,5R)-6-benzyloxy-7-oxo-1,6-diaza-bicyclo[3.2.1]octane-2-carboxylic acid and a process for its preparation is disclosed.

8 Claims, 1 Drawing Sheet

X-ray powder diffraction pattern
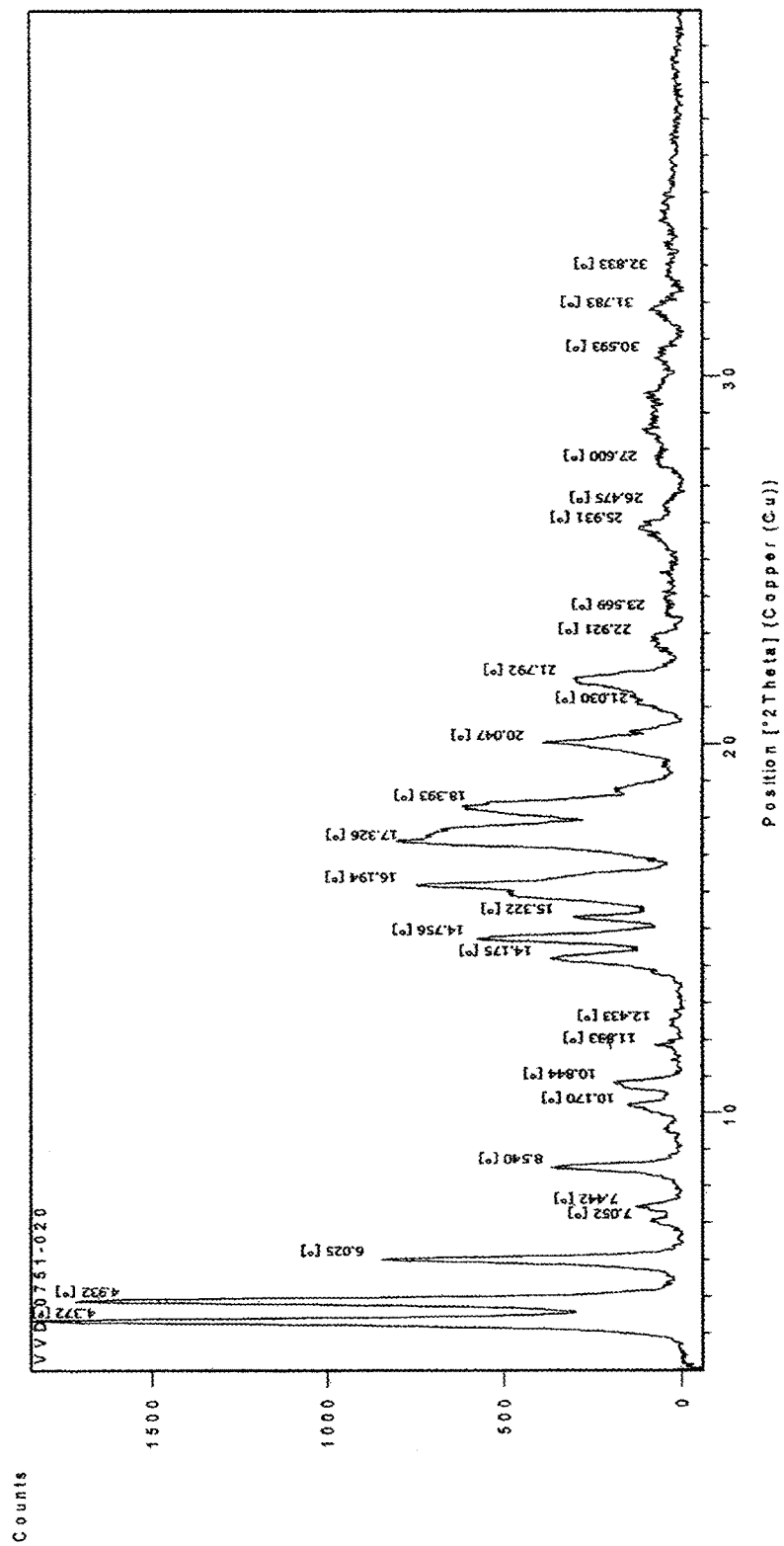

SODIUM SALT OF (2S, 5R)-6-BENZYLOXY-7-OXO-1,6-DIAZA-BICYCLO [3.2.1] OCTANE-2-CARBOXYLIC ACID AND ITS PREPARATION

RELATED PATENT APPLICATIONS

This application claims benefit of Indian Patent Application No. 699/MUM/2013 filed on Mar. 8, 2013, the disclosures of which are incorporated herein by reference in its entirety as if fully rewritten herein. All references including patents, patent applications, and literature cited in the specification are expressly incorporated herein by reference in their entirety.

FIELD OF THE INVENTION

The invention relates to a sodium salt of (2S,5R)-6-benzyloxy-7-oxo-1,6-diaza-bicyclo[3.2.1]octane-2-carboxylic acid and a process for its preparation.

BACKGROUND OF THE INVENTION

A compound of Formula (V), chemically known as (2S, 5R)-6-benzyloxy-7-oxo-1,6-diaza-bicyclo[3.2.1]octane-2-carboxylic acid, can be used as an intermediate in the synthesis of several antibacterial compounds, such as those disclosed in PCT International Patent Application No PCT/FR01/02418, PCT/US2009/031047, PCT/IB2012/054290 and PCT/IB2012/054296.

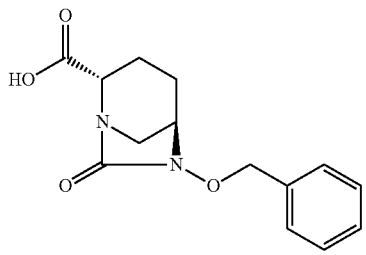

Formula (V)

The compound of Formula (V) i.e. (2S,5R)-6-benzyloxy-7-oxo-1,6-diaza-bicyclo[3.2.1]octane-2-carboxylic acid is disclosed in International Patent Application No. PCT/FR01/02418. Attempts to prepare this compound indicated that it was unstable and syrupy in nature and decomposed on storage. US Patent Publication No. 20100197928 discloses a procedure to prepare a diastereomeric mixture of (S)-5-benzyloxyamino-piperidin-2-carboxylic acid benzyl ester as an oxalate salt in 50:50 ratio.

Since the compound of Formula (V) is an important intermediate in the synthesis of several antibacterial agents, it was desired to have it exist in a stable form. The present inventors have now surprisingly discovered that a sodium salt of (2S,5R)-6-benzyloxy-7-oxo-1,6-diaza-bicyclo[3.2.1]octane-2-carboxylic acid (compound of Formula (I)) can be prepared and has several advantageous properties, including stability on storage.

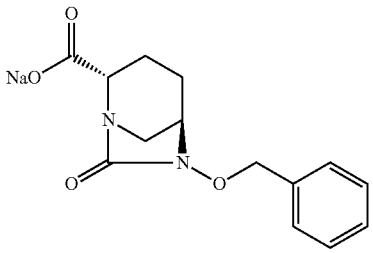

Formula (I)

SUMMARY OF THE INVENTION

In one general aspect, there is provided a compound of Formula (I):

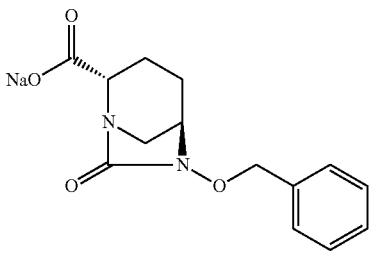

Formula (I)

In another general aspect, there is provided a compound of Formula (I) in a crystalline form.

In another general aspect, there is provided a process for preparation of a compound of Formula (I), comprising:

(a) reducing a compound of Formula (II) to a compound of Formula (III) in presence of sulfuric acid and sodium triacetoxy borohydride;

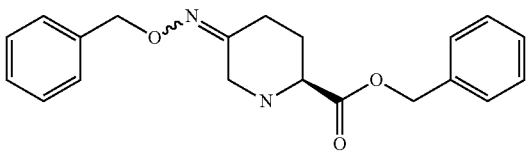

Formula (II)

Formula (III)

(b) cyclizing a compound Formula (III) to a compound of Formula (IV) in presence of triethylamine, triphosgene and N,N dimethyl pyridine;

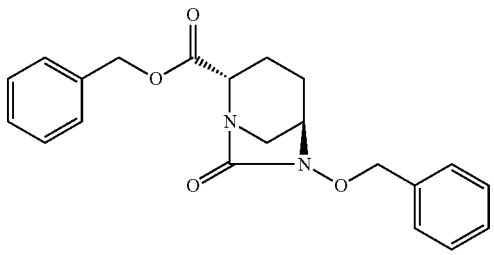

Formula (IV)

(c) hydrolyzing a compound of Formula (IV) to a compound of Formula (V) in presence of LiOH and HCl; and

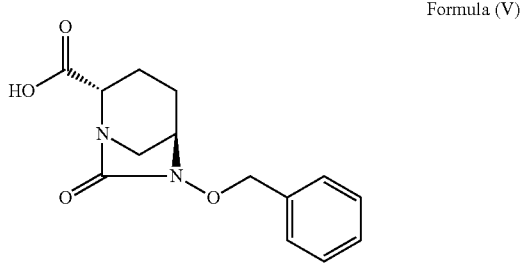 [SMILES: O=C(O)[C@@H]1CC[C@@H]2CN1C(=O)N2OCc1ccccc1]

Formula (V)

(d) converting a compound of Formula (V) to a compound of Formula (I) in presence of sodium 2-ethyl hexanoate.

The details of one or more embodiments of the invention are set forth in the description below. Other features, objects and advantages of the invention will be apparent from the following description including claims.

BRIEF DESCRIPTION OF THE DRAWINGS

FIG. 1—represents X-ray powder diffraction pattern of the crystalline form of sodium salt of (2S, 5R)-6-benzyloxy-7-oxo-1,6-diaza-bicyclo[3.2.1]octane-2-carboxylic acid.

DETAILED DESCRIPTION OF THE INVENTION

Reference will now be made to the exemplary embodiments, and specific language will be used herein to describe the same. It should nevertheless be understood that no limitation of the scope of the invention is thereby intended. Alterations and further modifications of the inventive features illustrated herein, and additional applications of the principles of the invention as illustrated herein, which would occur to one skilled in the relevant art and having possession of this disclosure, are to be considered within the scope of the invention. It must be noted that, as used in this specification and the appended claims, the singular forms "a," "an," and "the" include plural referents unless the content clearly dictates otherwise. All references including patents, patent applications, and literature cited in the specification are expressly incorporated herein by reference in their entirety as if fully rewritten herein.

In one general aspect, there is provided a compound of Formula (I):

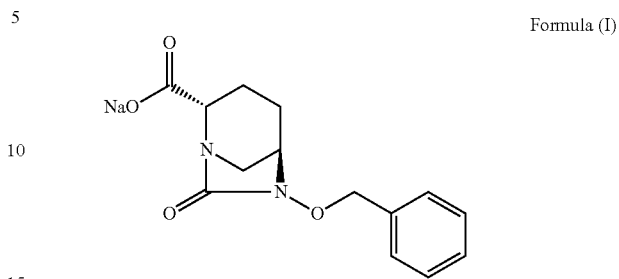

Formula (I)

In another general aspect, there is provided a process for preparation of a compound of Formula (I), comprising:

(a) reducing a compound of Formula (II) to a compound of Formula (III) in presence of sulfuric acid and sodium triacetoxy borohydride;

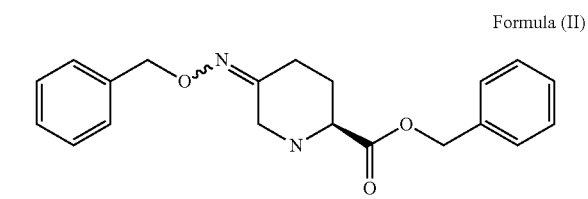

Formula (II)

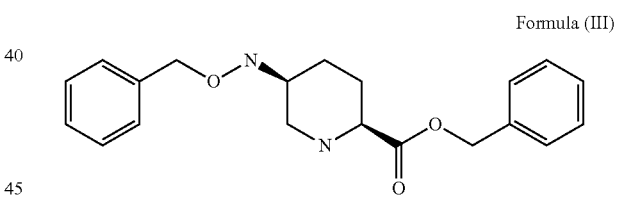

Formula (III)

(b) cyclizing a compound Formula (III) to a compound of Formula (IV) in presence of triethylamine, triphosgene and N,N dimethyl pyridine;

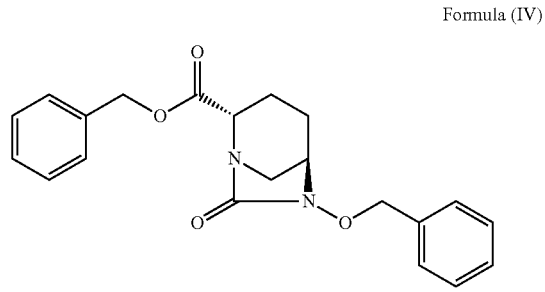 [SMILES: O=C(OCc1ccccc1)[C@@H]1CC[C@@H]2CN1C(=O)N2OCc1ccccc1]

Formula (IV)

(c) hydrolyzing a compound of Formula (IV) to a compound of Formula (V) in presence of LiOH and HCl; and

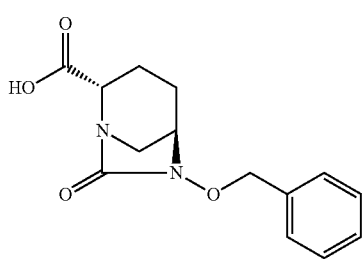

Formula (V)

(d) converting a compound of Formula (V) to a compound of Formula (I) in presence of sodium 2-ethyl hexanoate.

The process for preparation of a compound of Formula (I) is also described in Scheme 1.

In some embodiments, in the process for preparation of a compound of Formula (I) as described herein, the hydrolysis of a compound of Formula (IV) to a compound of Formula (V) is carried out at a temperature between about −15° C. to about −20° C.

In some other embodiments, the process for preparation of a compound of Formula (I) as described herein further comprises a step of purifying a compound of Formula (III) by preparing its oxalate salt.

In some embodiments, there is provided a compound of Formula (I) in a crystalline form.

In some other embodiments, the compound of Formula (I) has an X-ray powder diffraction pattern comprising a peak selected from the group consisting of 4.37 (±0.2), 4.93 (±0.2), 6.02 (±0.2), 8.54 (±0.2), 14.75 (±0.2), 16.19 (±0.2), 17.32 (±0.2), and 18.39 (±0.2) degrees 2 theta.

In some other embodiments, the compound of Formula (I) has an X-ray powder diffraction pattern comprising a peak selected from the group consisting of 4.37 (±0.2), 4.93 (±0.2), 6.02 (±0.2), 8.54 (±0.2), 10.17 (±0.2), 10.84 (±0.2), 14.17 (±0.2), 14.75 (±0.2), 15.32 (±0.2), 16.19 (±0.2), 17.32 (±0.2), 18.39 (±0.2), 20.05 (±0.2), and 21.79 (±0.2) degrees 2 theta.

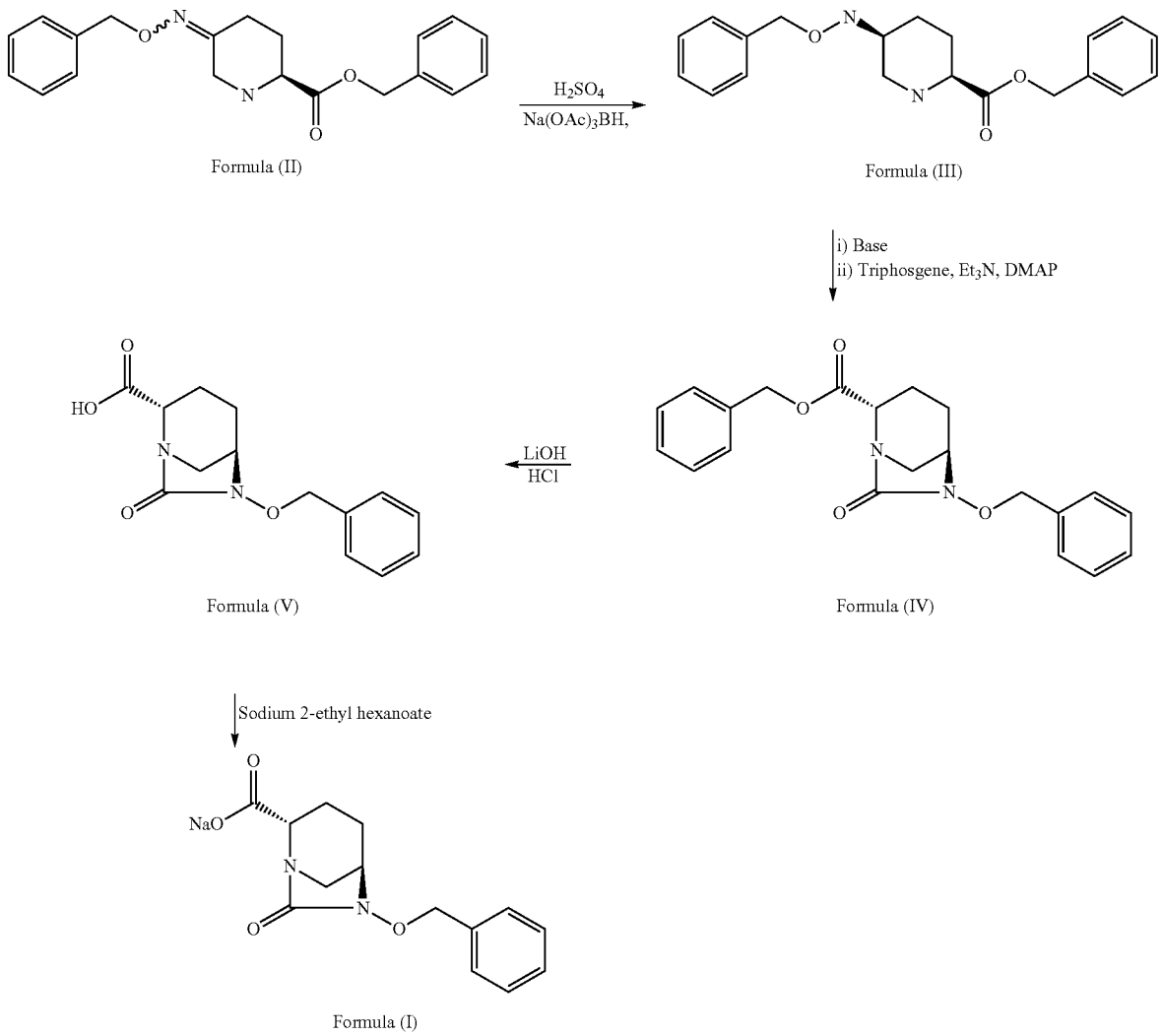

Scheme - 1

In some embodiments, the compound of Formula (I) has an X-ray powder diffraction pattern substantially the same as shown in FIG. 1.

In some embodiments, the compound of Formula (I) has a purity of at least 98% as determined by HPLC.

The compound of Formula (I) according to the invention has several advantageous properties, which include the following:

(1) The compound of Formula (I) is isolable as a highly pure solid material (purity of about at least 98% as determined by HPLC) and is a non-hygroscopic material as compared with the corresponding free acid (compound of Formula (V), which is obtained as syrupy material).

(2) The compound of Formula (I) is surprisingly stable on storage. For example, in a typical stability study, the compound of Formula (I) on storage at room temperature for three months exhibited excellent stability (purity as analyzed by HPLC, initial purity 99.75%; purity after two moths: 99.69%; and purity after three months: 99.66%).

(3) The compound of Formula (I) is easy to isolate, store and handle during further reaction sequences.

It will be readily apparent to one skilled in the art that varying substitutions and modifications may be made to the invention disclosed herein without departing from the scope and spirit of the invention. For example, those skilled in the art will recognize that the invention may be practiced using a variety of different compounds within the described generic descriptions.

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Example 1

Preparation of Sodium Salt of (2S,5R)-6-benzyloxy-7-oxo-1,6-diaza-bicyclo[3.2.1]octane-2-Carboxylic Acid Step-1: Preparation of 5-benzyloxyamino-piperidin-2-carboxylic acid benzyl ester's oxalate salt (2S,5R) and (2S,5S)

To a four neck (10 L) round bottom flask was charged sodium borohydride (50.26 gm, 1.329 mol) followed by ethyl acetate (2.25 L). The suspension was cooled to about 0° C. by using ice-salt mixture and to this acetic acid (230 ml, 3.98 mol) was added drop-wise over a period of 1 hour by maintaining temperature below 0° C. under stirring. After the addition, the cooling was removed and the reaction mixture was allowed to warm gradually to about 20° C. to 25° C. The white suspension (sodium triacetoxy borohydride) thus obtained was stirred for 4 hours at about 20° C. to 25° C.

To another 20 L round bottom flask was charged E/Z mixture of (S)-5-benzyloxyimino-piperidin-2-carboxylic acid benzyl ester (225 gm, 0.665 mol, prepared using a procedure described in US Patent Publication No. 2010/0197928) followed by ethyl acetate (1.125 L). The reaction mixture was cooled under stirring to −10° C. and concentrated sulfuric acid (180 ml, 3.32 mol) was added by maintaining temperature below −5° C. The mixture was stirred for additional 30 minutes at −10° C. to obtain a clear solution. To the clear solution was added white suspension (sodium triacetoxy borohydride) prepared above via addition funnel while maintaining temperature below −5° C. The resulting suspension was stirred for 1 hour at −10° C. The reaction mixture thus obtained was quenched by adding aqueous potassium hydrogen carbonate solution (prepared from 837 gm, 8.37 mol in 3.5 L water) while maintaining the temperature at about −10° C. to 10° C. The reaction mixture was stirred for 30 minutes and warmed to 25° C. The organic layer was separated and aqueous layer was extracted with ethyl acetate (1 L). The combined organic layer was washed with water (2 L) followed by saturated aqueous sodium chloride solution (1 L). The organic layer was evaporated under vacuum to provide a crude compound of Formula (III) as an oily mass in 204 gm quantity.

The oily mass (204 gm, 0.59 mol) obtained above was dissolved in ethyl acetate (800 ml) under stirring and a solution of oxalic acid (83 gm, 0.66 mol) in ethyl acetate (410 ml) and acetone (410 ml) mixture, was added drop-wise within 1 hour. The precipitated solid was stirred for 4 hours at 25° C. It was then filtered under suction and the wet cake thus obtained was washed with 1:1 v/v ethyl acetate acetone mixture (400 nil). The solid was dried by air to provide title intermediate compound (oxalate salt of 5-benzyloxyamino-piperidin-2-carboxylic acid benzyl ester) in 210 gm quantity in 73.6% yield as a pale yellow solid, and had the following analysis:

Analysis

NMR (DMSO-$d_6$) (major diastereomer's chemical shifts are mentioned)

7.25-7.40 (m, 10H), 5.22 (s, 2H), 4.56 (s, 2H), 4.05 (dd, 1H), 3.38 (dd, 1H), 3.12-3.17 (m, 2H), 2.66 (t, 1H), 2.15 (dd, 1H), 1.84-1.89 (m, 2H), 1.69-1.79 (m, 1H), 1.39-1.69 (m, 1H).

Mass $C_{20}H_{24}N_2O_3 \cdot C_2H_2O_4$: 341.3 as M+1 for free base.

Diastereomeric purity by HPLC: 75.99 and 20.99

Step-2: Preparation of free base of 5-benzyloxyamino-piperidin-2-carboxylic acid benzyl ester in (2S,5R) and (2S,5S)

To the diastereomeric mixture of oxalate salt of benzyl 5-benzyloxyamino-piperidin-2-carboxylate (204 gm, 0.474 mol) obtained in Step-1 above, was added a mixture of ethyl acetate (2 L) and distilled water (1 L) under stirring at room temperature to obtain a clear solution. To the reaction mixture was added 8% aqueous sodium bicarbonate solution (prepared from 80 gm of sodium bicarbonate, 0.952 mol, and 1 L water) under stirring within 20 minutes. The resulting mixture was stirred for 2.5 hours. The organic layer was separated and aqueous layer was extracted with ethyl acetate (800 ml×2). Combined organic layer was washed successively with water (1 L) and brine (1 L). Organic layer was dried over sodium sulfate. Solvent was evaporated under vacuum to provide 164 gm free base as viscous oil in quantitative yield. It was used as such for the next reaction.

Step-3: Preparation of 7-benzyloxy-7-oxo-1,6-diaza-bicyclo[3.2.1]octane-2-carboxylic acid benzyl ester in (2S,5R) and (2S,5S)

The benzyl 5-benzyloxyamino-piperidin-2-carboxylate free base (164 gm, 0.484 mol) was dissolved in acetonitrile (2.5 L) to provide a clear solution under stirring. To the reaction mixture was added triethyl amine (175 ml, 1.26 mol) under stirring at room temperature. To this, was added slowly a solution of triphosgene (64 gm, 0.212 mol) in acetonitrile (640 ml) by maintaining the temperature of reaction mixture below 30° C. during addition. The resulting yellow suspension was stirred for 30 minutes at room temperature. N,N-dimethyl pyridine (DMAP) (5.91 gm, 0.0484 mol) was added to the suspension and the reaction mixture was allowed to stir for 16 hours.

The reaction mixture was quenched by saturated aqueous sodium bicarbonate solution (1.32 L). Fall in temperature was observed upon addition of saturated aqueous sodium bicarbonate solution till 13° C. Stirring was continued for 30 minutes after addition. Reaction mixture was concentrated as such under vacuum to remove acetonitrile till distillation of water starts. To the resulting mixture was added additional distilled water (1.65 L) under stirring. Aqueous layer was extracted twice with dichloromethane (1.7 L and 850 ml). Combined organic layer was washed with water (850 ml) followed by brine (850 ml). Organic layer was dried over sodium sulfate. Solvent was evaporated under vacuum to yield diastereomeric mixture of 6-benzyloxy-7-oxo-1,6-diaza-bicyclo{3.2.1}-octane-2-carboxylic acid benzyl ester (2S,5R) and (2S,5S) in 76.38:16.37 by HPLC in 169 gm quantity (97%) as a viscous oil. This intermediate was prone for generating impurities and hence, was stored below 4° C. temperature overnight.

Analysis

Mass: $C_{21}H_{22}N_2O_4$: 367.2 as M+1.

Diastereomeric purity by HPLC: 76 and 16

Step-4: Preparation of (2S,5R)-7-benzyloxy-7-oxo-1,6-diaza-bicyclo[3.2.1]octane-2-carboxylic acid The diastereomeric mixture of 6-benzyloxy-7-oxo-1,6-diaza-bicyclo{3.2.1}-octane-2-carboxylic acid benzyl ester in 76:16 ratio obtained as above in Step-3 (100 gm, 0.273 mol) was dissolved in acetone (2 L) under stirring at room temperature. The clear solution was cooled to −20° C. and to it was added a solution of lithium hydroxide (14 gm, 0.333 mol) in water:acetone mixture (800 ml:270 ml) by maintaining reaction temperature between −15° C. to −20° C. over a period of 3 hours under stirring. Stirring was continued further for 1.5 hours. After this, pH of the reaction mixture was adjusted to 8 by adding 2N aqueous hydrochloric acid while maintaining the temperature between −15° C. to −20° C. under stirring. Thereafter, the reaction mixture was allowed to warm to 25° C. to 30° C. Brine (300 ml) was added to the reaction mixture and the aqueous layer was separated. The aqueous layer was extracted with toluene (1 L and 500 ml×2). The pH of the aqueous layer was adjusted to 2 by adding 2N aqueous hydrochloric acid. Aqueous layer was extracted with dichloromethane (500 ml×3). Combined organic layer was dried over sodium sulfate. Solvent was evaporated under vacuum below 40° C. to provide title intermediate compound as viscous oil in 51 gm quantity in 97.5:1.2 ratio as determined by HPLC, in 68% yield. This was used immediately for the next reaction step.

Analysis:

NMR (CDCl$_3$)

7.33-7.41 (m, 5H), 5.03 (d, 1H), 5.87 (d, 1H), 4.08 (d, 1H), 3.32 (br s, 1H), 3.07 (br d, 1H), 2.91 (d, 1H), 1.82-2.76 (m, 3H), 1.59-1.70 (m, 1H).

Mass: $C_{14}H_{16}N_2O_4$: 275.2 as M−1.

Diastereomeric purity by HPLC: 97.5 and 1.2

Step-5: Sodium salt of (2S,5R)-6-benzyloxy-7-oxo-1,6-diaza-bicyclo{3.2.1}-octane-2-carboxylic acid To a four neck (5 L) round bottom flask, equipped with mechanical stirrer and thermometer pocket was charged (2S,5R)-6-benzyloxy-7-oxo-1,6-diaza-bicyclo{3.2.1}-octane-2-carboxylic acid obtained in Step-4 above (200 gm, 0.725 mol) along with acetone (2 L) under nitrogen atmosphere and stirring was started at room temperature to provide a clear solution. To the clear solution, was added a solution of sodium 2-ethyl hexanoate (132.34 gm, 796 mmol) in 1 L acetone via addition funnel for next 30 minutes. The reaction mixture was stirred for 16 hours at 25° C. to 30° C.

The precipitated solid was filtered under suction and the wet cake was washed with chilled acetone (400 ml). The non-hygroscopic solid was dried under vacuum at 40° C. for 1 hour to provide off-white colored material (sodium salt of (2S,5R)-6-benzyloxy-7-oxo-1,6-diaza-bicyclo{3.2.1}-octane-2-carboxylic acid) in 135 gm (89%, calculation adjusted for 70% purity of free acid) quantity.

Analysis:

NMR (DMSO-d$_6$)

7.32-7.43 (m, 5H), 4.88 (q, 2H), 3.49 (s, 1H), 3.21 (d, 1H), 2.73 (d, 1H), 2.04-2.09 (m, 2H), 1.74-1.77 (m, 1H), 1.65-1.72 (m, 1H), 1.55-1.60 (m, 1H).

Mass: $C_{14}H_{15}N_2O_4$.Na: 275.2 as M−1 (for acid).

Purity as determined by HPLC: 99.8%.

X-Ray Powder Diffraction Pattern: as given in FIG. 1

X-ray powder diffraction pattern exhibited major peaks at the following 2 theta values:

4.37 (±0.2), 4.93 (±0.2), 6.03 (±0.2), 8.54 (±0.2), 10.17 (±0.2), 10.84 (±0.2), 14.17 (±0.2), 14.76 (±0.2), 15.32 (±0.2), 16.19 (±0.2), 17.33 (±0.2), 18.39 (±0.2), 20.05 (±0.2), and 21.79 (±0.2).

Typical X-ray analysis was performed as follows. Pass the test substance through sieve #100 BSS or gently grind it with a mortar and pestle. Place the test substance uniformly on a sample holder having cavity surface on one side, press the sample and cut into thin uniform film using a glass slide in such a way that the surface of the sample should be smooth and even. Record the X-ray diffractogram using the following instrument parameters.

| Instrument | X-Ray Diffractometer (PANalytical, Model X'Pert Pro MPD) |
|---|---|
| Target source | Cu k (α) |
| Anti-scattering slit (Incident beam) | 1° |
| Programmable Divergent slit | 10 mm (fixed) |
| Anti-scattering slit (Diffracted beam) | 5.5 mm |
| Step width | 0.02° |
| Voltage | 40 kV |
| Current | 40 mA |
| Time per step | 30 seconds |
| Scan range | 3 to 40° |

We claim:
1. A compound of Formula (I):

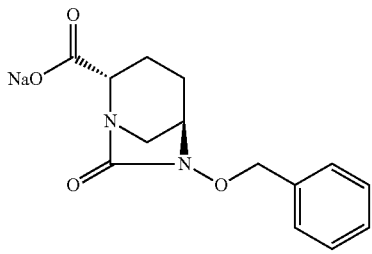

Formula (I)

having an X-ray powder diffraction pattern comprising a peak selected from the group consisting of 4.37 (±0.2), 4.93 (±0.2), 6.02 (±0.2), 8.54 (±0.2), 14.75 (±0.2), 16.19 (±0.2), 17.32 (±0.2), and 18.39 (±0.2) degrees 2 theta.

2. A compound according to claim 1 in a crystalline form.

3. A compound according to claim 1, having an X-ray powder diffraction pattern comprising a peak selected from the group consisting of 10.17 (±0.2), 10.84 (±0.2), 14.17 (±0.2), 15.32 (±0.2), 20.05 (±0.2), and 21.79 (±0.2) degrees 2 theta.

4. A compound according to claim 1, having an X-ray powder diffraction pattern substantially the same as shown in FIG. 1.

5. A process for preparation of a compound of Formula (I) according to claim 1, comprising:
 (a) reducing a compound of Formula (II) to a compound of Formula (III) in presence of sulfuric acid and sodium triacetoxy borohydride;

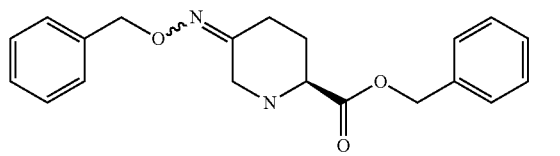

Formula (II)

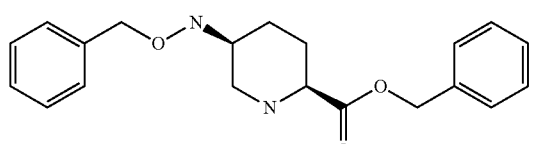

Formula (III)

(b) cyclizing a compound Formula (III) to a compound of Formula (IV) in presence of triethylamine, triphosgene and N,N dimethyl amino pyridine;

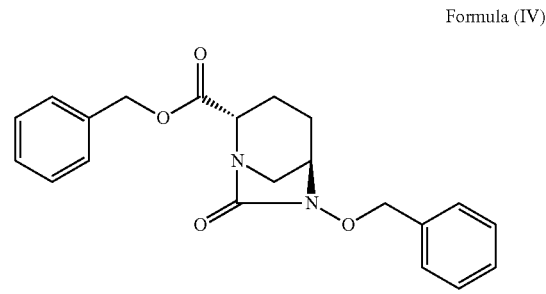 [SMILES: O=C(OCc1ccccc1)[C@@H]1CC[C@@H]2CN1C(=O)N2OCc1ccccc1]

Formula (IV)

(c) hydrolyzing a compound of Formula (IV) to a compound of Formula (V) in presence of LiOH and HCl; and

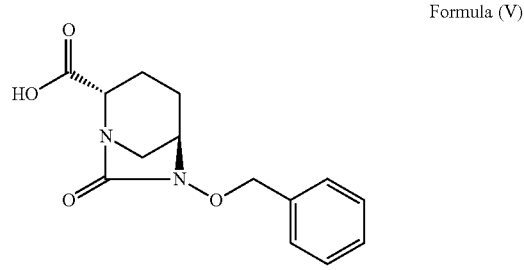 [SMILES: O=C(O)[C@@H]1CC[C@@H]2CN1C(=O)N2OCc1ccccc1]

Formula (V)

(d) reacting a compound of Formula (V) with sodium 2-ethyl hexanoate;
 (e) isolating the compound of Formula (I) in a crystalline form.

6. A process according to claim 5, wherein the hydrolysis of a compound of Formula (IV) to a compound of Formula (V) is carried out at a temperature between about −15° C. to about −20° C.

7. A process according to claim 5, further comprising a step of purifying a compound of Formula (III) by preparing its oxalate salt.

8. A compound according to any of the claims 1, 2, 3, or 4, having a purity of at least 98% as determined by HPLC.

* * * * *

UNITED STATES PATENT AND TRADEMARK OFFICE
CERTIFICATE OF CORRECTION

PATENT NO.        : 9,862,718 B2
APPLICATION NO.   : 14/770960
DATED             : January 9, 2018
INVENTOR(S)       : Vikas Vitthalrao Deshmukh et al.

It is certified that error appears in the above-identified patent and that said Letters Patent is hereby corrected as shown below:

In the Specification

On Column 2, Lines 57-64, the chemical structure of Formula (III) reads:

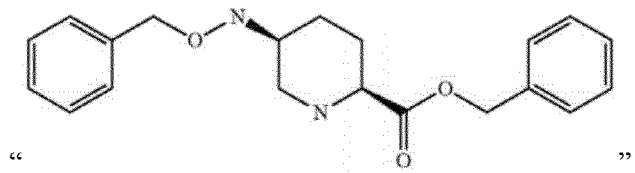

"                                    "

Should read:

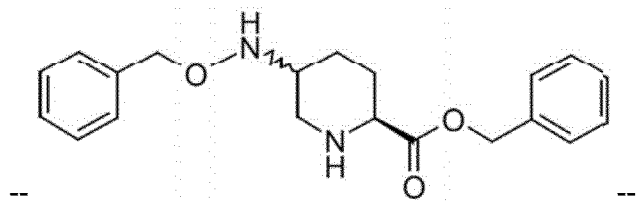

--                                   --

On Column 4, Lines 40-45, the chemical structure of Formula (III) reads:

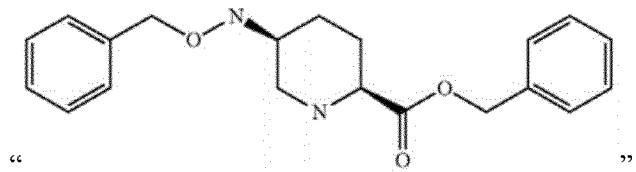

"                                    "

Should read:

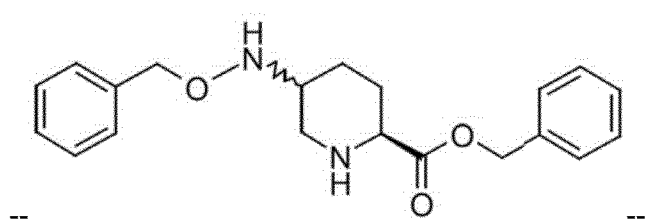

--                                   --

Signed and Sealed this
Second Day of October, 2018

Andrei Iancu
*Director of the United States Patent and Trademark Office*

CERTIFICATE OF CORRECTION (continued)

On Column 6, in "Scheme-1" Section, under Line 19, the chemical structure of Formula (III) reads:

"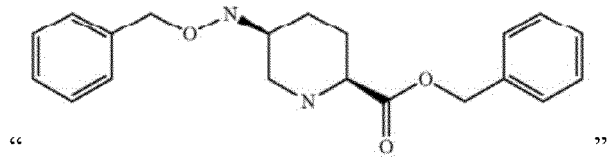"

Should read:

-- 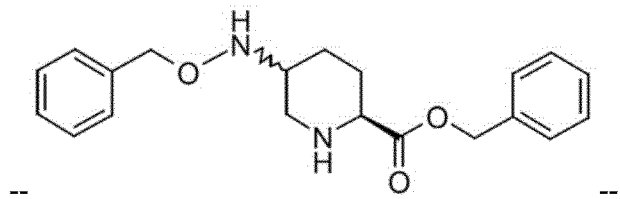 --